United States Patent [19]

Ponnet

[11] Patent Number: 5,500,163
[45] Date of Patent: Mar. 19, 1996

[54] MATERIAL AND SPLINT FOR ORTHOPAEDICAL, SURGICAL AND VETERINARY USE AND METHOD OF MAKING SAME

[76] Inventor: Tom P. M. G. Ponnet, Statiestraat 92, B-2600 Antwerp, Belgium

[21] Appl. No.: 157,146

[22] PCT Filed: Jun. 16, 1992

[86] PCT No.: PCT/EP92/01368

§ 371 Date: Dec. 7, 1993

§ 102(e) Date: Dec. 7, 1993

[87] PCT Pub. No.: WO93/00117

PCT Pub. Date: Jan. 7, 1993

[30] Foreign Application Priority Data

Jun. 24, 1991 [NL] Netherlands ............. 9101082

[51] Int. Cl.$^6$ ................................................. B29C 35/02
[52] U.S. Cl. ............. 264/473; 264/45.1; 264/53; 264/131; 264/211.12; 264/328.1; 264/236; 264/478; 602/5; 602/6
[58] Field of Search ................. 264/22, 129, 131, 264/233, 236, 45.1, 53, 211.12, 328.1; 602/5, 6, 8

[56] References Cited

U.S. PATENT DOCUMENTS

| 3,692,023 | 9/1972 | Phillips et al. | 602/7 |
| 4,175,177 | 11/1979 | Potts | 528/354 |
| 4,427,003 | 1/1984 | Fennimore et al. | 602/8 |
| 4,433,680 | 2/1984 | Yoon | 602/8 |
| 4,473,671 | 9/1984 | Green | 523/105 |
| 4,784,123 | 11/1988 | Robeson | 602/8 |
| 4,852,557 | 8/1989 | Grim | 602/8 |
| 4,960,116 | 10/1990 | Milner | 602/8 |
| 5,019,096 | 5/1991 | Fox, Jr. et al. | 623/1 |
| 5,151,315 | 9/1992 | Ponnet | 428/212 |

FOREIGN PATENT DOCUMENTS

| 0090289 | 10/1983 | European Pat. Off. | 602/8 |
| 1175854 | 7/1989 | Japan | 602/8 |
| 2207141 | 1/1989 | United Kingdom | 602/8 |

*Primary Examiner*—Allan R. Kuhns
*Attorney, Agent, or Firm*—William A. Drucker

[57] ABSTRACT

A thermoplastic material, mainly to be used for splints and supports in orthopaedical, surgical and veterinary practice, is proposed for the fixation of body parts, the material including a copolymer of ε-caprolactone, polyurethane, and ethylene-butylene-styrene mixed with triallylcyanurate and oleic acid-imide, the copolymer mixture being gamma irradiated after processing, such that a degree of cross-linking of the molecules and a partially crystalline configuration results in a molded material with reproducible flexibility, elasticity and reciprocal stretch properties.

5 Claims, No Drawings

MATERIAL AND SPLINT FOR ORTHOPAEDICAL, SURGICAL AND VETERINARY USE AND METHOD OF MAKING SAME

The present invention relates to a thermoplastic polymer material to be applied for orthopaedical, surgical and veterinary use, shaped as splints, artificial parts, prothesis, bandages and dressings.

The material ought to be used in suitable shapes for said practices as a supporting gird or splint and it shall comply with special requirements, which are not claimed for other plastic articles.

Polymer plastic materials have been proposed already for similar purposes, in order to forestall the disadvantages of gypsum splints.

In U.S. Pat. No. 3,692,023 polymers or mixtures of poly-ε-caprolactone and polyvinylethylether are described, which can be put upon fabric or gauze. This material was to be wrapped, in a warmed condition, around broken limbs, and after cooling down it formed a relatively hard supporting means, which could be removed again manually by warming up same.

In U.S. Pat. No. 4,175,177 orthopaedical bandages were described, consisting of copolymers of ε-caprolactone and acrylates.

Now more suitable materials have been sought in order to control the flexibility, bending strength, reciprocal elasticity and tensile strength in a reproducible manner.

The materials, which are already known, have been studied and compared with each other.

From these investigations it became apparent, that the following requirements should be met merely in an accurate way:

1. Application of a thermoplastic polymer without any supporting material.
2. The material must have the property to be deformed easily.
3. The material shall be fit for repeated use.
4. The material should have a high compression strength.
5. The material should have a defined elasticity.
6. The material should have a resistance to remaining elongation.

The phenomena of elasticity and resistance to elongation, as well as the compression strength, depend from the degree of crystallinity, the cross-linking index and the shape of the molecular chains.

A suitable material for surgical and orthopaedical practice, consisting of a composite of layers of poly-ε-caprolactone and a polyester with an upper layer of polyurethane foam with open cells has been described in European patent 0 263 552 of applicant.

A novel mixture of improved copolymers with a plasticizer has now been developed.

Hereby use was made of insight and further reflections on the structure of materials obtained by fundamental research. The structure of the materials is shown on page 5.

The process to obtain the present material according to the invention is characterized by a copolymerization by heating equimolecular weight-quantities of ε-caprolactone, polyurethane of polyoxypropylene-glycol and toluene-di-isocyanate with ethylene-butylene-styrene-copolymer, while during the formation of this mixed copolymer triallyl-cyanurate in an amount of 0.3 to 3.5% wt./wt., related to the total mass, and about 1% wt./wt. of oleic acid imide as a plasticizer are added, and the product, cast in shapes of block sections or sheeting is then irradiated by Gammaradiation up to 2.5 Megarad during a short period.

By this method a material is obtained, which by its partial cross-linking of bundles of macromolecular chains with an isotactic structure and its partial crystallinity of 5–10% can be processed successfully in injection moulds with an inner coating of polytetrafluorethylene, to obtain desired shapes for practical surgery and orthopaedy.

To a small part of the above raw materials during the last step some water can be added, such that a soft foamed layer with open cells is formed, which at the elevated temperature is attaching to the surface of the shapes in a thickness of 0.5 to 1.0 mm.

The temperature of the copolymerization reaction is ranging from 45° to 180° C., depending from the plasticizer contents.

The elasticity, crystallinity and stretch properties depend from the enthalpy of deformation. A measure for this quantity has been developed by Mooney and Rivlin, described in "Journal of Applied Physics", Vol. II, (1940), pages 582 a.f.

A review of the evaluation of similar materials is represented in "Elasticity and Structure of Polyurethane Networks", Dissertation of R. Blokland, Delft Technical University, 1968.

A stretched elastomeric copolymer of the type of the present material has properties in accordance with the formula of Mooney and Rivlin:

$$F=(C_1+\lambda^{-1}\cdot C_2)\cdot(\lambda-\lambda^{-2}),$$

Wherein the following parameters appear:
F=strain force [dyn/cm$^2$]
$C_1$=constant for basic polymer [Kg/cm$^2$]
$C_2$=Constant for copolymer [Kg/cm$^2$]
λ=Stretch.
The enthalpy of deformation of each component is:

$$\Delta G=\tfrac{1}{2}\cdot C\cdot(\lambda_x^2+\lambda_y^2+\lambda_z^2-3)$$

wherein the symbols are the following:
ΔG=Enthalpy of deformation,
C=Constant of the component material,
$\lambda_x$=Stretch in x-direction,
$\lambda_y$=Stretch in y-direction,
$\lambda_z$=Stretch in z-direction.

The elastic deformation is leading to an increase of the crystallinity and of the enthalpy of deformation (decrease of the entropy).

For the polyurethane-copolymers with ethylene-butylene-styrene and caprolactone-components the values of the constants C at a standard temperature of 25° C. are as follows:
Basic polymer: $C_1$=3,30 Kg/cm$^2$
Copolymer: $C_2$=2,00 Kg/cm$^2$.

These values can be altered within ranges by the addition of the triallylcyanurate and of the oleic acid-imide, such that a variety of well-defined properties can be obtained.

By the gamma-irradiation a reverse effect to some extent is obtained, such that every desired mechanical property with this versatile polymer material according to the invention can be reached, which is very important for the medical treatment.

It is important that the shaped material in practice will remain at its place as required, that it will not slide or slip and that it will not deform if no pressure is applied, and moreover that it will not stick at the skin of the patient.

The material as developed according to the present invention has a so-called "plastic memory", resulting from its special molecular and crystalline structure, as described, such that after adaptation in the adjusted shape as a splint or support, it will have some suppleness at a slightly elevated temperature and that it presses softly at the part of the body, the limb or the organism in question.

The product is not restricted in its application to orthopaedical or surgical possibilities of use, but it might be used as well for technical purposes, such as the manufacture of filter aids, membranes and sieves, because it can be made porous and specifically permeable in thin layers. This renders the possibilty of use in specialized clinical and analytical apparatus.

Furthermore the possibility of recycling of the present material is important, because it can be reduced into the form of particles and it can be granulated and reshaped anew by extrusion and for injection moulding.

The present invention relates to the preparation, processing and applications of the described material.

For special paramedical applications, such as arch supports and suchlike or similar expedients, the polymer foam layer on the surface of the articles can be replaced partly or entirely by a surface treatment with a suspension of a neutral scourer, such as e.g. pumice powder.

The chemical structures of the organic building parts of the copolymer mixture are rendered in the enclosed formula sheet with formulae 1 to 5. The copolymer mixture is innocuous for human and animal tissue.

As polycaprolactone is an aerobic-biodegradable material, the compositions according to the present invention are explicitly compatible with the environment.

Sheet of formulae:

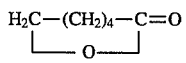   (1)

ε-caprolactone.

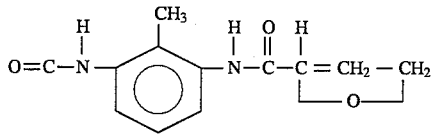   (2)

Polyoxypropylene-toluene-di-isocyanate.

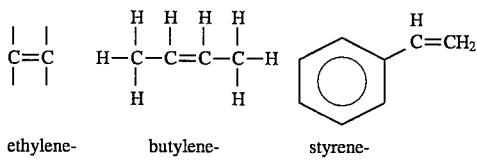   (3)

ethylene-   butylene-   styrene-

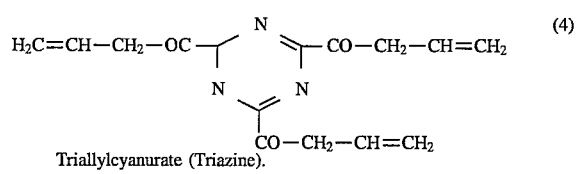   (4)

Triallylcyanurate (Triazine).

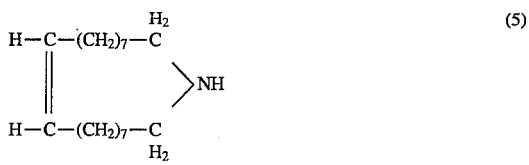   (5)

Oleic acid-imide (Oleimide).

I claim:

1. A method for the production of a deformable material for orthopaedical, surgical, veterinary and technical applications, based upon poly-ε-caprolactone, wherein equimolecular weight amounts of ε-caprolactone, polyurethane prepared of polyoxypropylene glycol and toluene-di-isocyanate, and ethylene-butylene-styrene-copolymer are reacted together under heating, and with reflux cooling of vapours during said reaction, triallylcyanurate in an amount of 0.3 to 3.5% wt./wt. and slowly oleic acid-imide in an amount of about 1% wt./wt. of the total mass are added, and the reaction product is cooled down, washed and granulated, and brought into the desired surgical or technical shape by injection moulding or extrusion, followed by irradiation with gamma rays of up to 2.5 Mrad, to obtain a solid flexible shape of flexibility and elasticity, as required for practical use.

2. A method for the manufacture of orthopaedical and surgical splint—or supporting means consisting of thermoplastic polymer material, wherein a shaped product obtained according to claim 1 is coated with a thin layer of a scourer.

3. A method for the manufacture of articles according to claim 2, wherein a thin layer of weak open-cell foam of polymer is spread upon the surface of the scourer.

4. Orthopaedical and surgical supporting means for the fixation of body parts after a fracture or an operation, wherein said means consist entirely of a material manufactured according to claim 2, or comprise partly such a material.

5. Orthopaedical and surgical supporting means for the fixation of body parts after a fracture or an operation, wherein said means consist entirely of a material manufactured according to claim 3.

* * * * *